United States Patent
Tseng et al.

(10) Patent No.: US 9,575,016 B2
(45) Date of Patent: Feb. 21, 2017

(54) PROJECTION METHOD OF THREE-DIMENSIONAL IMAGING

(71) Applicant: Institute of Nuclear Energy Research, Atomic Energy Council, Executive Yuan, R.O.C., Taoyuan (TW)

(72) Inventors: Fan-Pin Tseng, Taipei (TW); Meei-Ling Jan, Taoyuan (TW)

(73) Assignee: INSTITUTE OF NUCLEAR ENERGY RESEARCH, ATOMIC ENERGY COUNCIL, EXECUTIVE YUAN, R.O.C., Taoyuan (TW)

( * ) Notice: Subject to any disclaimer, the term of this patent is extended or adjusted under 35 U.S.C. 154(b) by 0 days.

(21) Appl. No.: 14/877,470

(22) Filed: Oct. 7, 2015

(65) Prior Publication Data
US 2016/0123900 A1    May 5, 2016

(30) Foreign Application Priority Data

Oct. 30, 2014  (TW) .............................. 103137642 A

(51) Int. Cl.
*G01N 23/04* (2006.01)
*G06T 11/00* (2006.01)

(52) U.S. Cl.
CPC ............ *G01N 23/04* (2013.01); *G01N 23/046* (2013.01); *G06T 11/005* (2013.01); *G06T 2211/416* (2013.01); *G06T 2211/424* (2013.01)

(58) Field of Classification Search
CPC ..... G01N 23/04; G01N 23/046; G06T 11/005; G06T 2211/416; G06T 2211/424
USPC .................................. 382/128, 131, 133, 154
See application file for complete search history.

(56) References Cited

U.S. PATENT DOCUMENTS

| | | | | | |
|---|---|---|---|---|---|
| 5,412,703 | A | * | 5/1995 | Goodenough | G01N 23/046 378/4 |
| 6,002,739 | A | * | 12/1999 | Heumann | G06T 11/006 378/21 |
| 6,178,223 | B1 | * | 1/2001 | Solomon | A61B 6/02 378/15 |
| 6,201,850 | B1 | * | 3/2001 | Heumann | G01B 15/025 378/22 |
| 2011/0097007 | A1 | * | 4/2011 | Zeng | G06T 11/006 382/260 |
| 2011/0220794 | A1 | * | 9/2011 | Censor | G01N 23/046 250/307 |

* cited by examiner

*Primary Examiner* — Tom Y Lu
(74) *Attorney, Agent, or Firm* — Locke Lord LLP; Tim Tingkang Xia, Esq.

(57) ABSTRACT

A projection method of three-dimensional imaging includes the steps of respectively projecting a radiation field emitted from a radiation source with respect to one specific detector of a plurality of detectors and a three-dimensional sub-voxel onto two two-dimensional planes; rotating the specific detector to one specific axis of the two dimensional plane; performing a calculation for obtaining a sub-geometric factor corresponding to each specific detector and each voxel; and, finally, forming a geometric factor by combining each sub-geometric factor defined by each detector and each voxel.

9 Claims, 14 Drawing Sheets

PROJECTION METHOD OF THREE-DIMENSIONAL IMAGING

CROSS-REFERENCE TO RELATED APPLICATIONS

This application claims the benefit of Taiwan Patent Application Serial No. 103137642, filed Oct. 30, 2014, the subject matter of which is incorporated herein by reference.

BACKGROUND OF INVENTION

1. Field of the Invention

The invention relates to a projection method of three-dimensional imaging, and more particularly to the projection method of three-dimensional imaging applied to the field of the radiological medicine.

2. Description of the Prior Art

As the technology progresses, imaging in the radiological medicine has become an effective diagnostic tool. The imaging is executed firstly by building an appropriate numerical model that satisfies the related physical phenomena, and then by reconstructing a relevant three-dimensional (3D) image through image-reconstruction algorithms. Popular imaging methods nowadays include the computed tomography (CT), the positron emission tomography (PET), the single-photon emission computed tomography (SPECT) and the like.

In the history of image-reconstruction algorithms, early analytical methods include the filtered back projection (FBP), the matrix inversion tomosynthesis (MITS) and so on. Recently, as the rapid development in computer and hardware technology, the iterative techniques for achieving high-resolution imaging quality such as the maximum likelihood expectation maximization (MLEM), the ordered subset expectation maximization (OSEM), the algebraic reconstruction technique (ART), the projection onto convex sets (POCS) and the like re-construction algorithms become the mainstream. However, in order to obtain further better imaging quality, more precise systematic matrix models shall be introduced for the calculations of the iterative reconstruction.

By having the computed tomography for example, the imaging device receives signals and then transfers the signals into a discrete matrix. The discrete matrix that is then stored in the computer as a mathematic model for image reconstruction can be expressed as follows.

$$[G]_{m \times n}[\bar{f}]_{n \times 1} = [\bar{C}]_{m \times 1}$$

where vector C (m×1) is the received signal in a discrete form stored in the computer, matrix G is the system matrix (m×n), and vector f(n×1) is the 3D image to be solved. Knowing that the photon travels straightly and neglecting other physical factors such as scattering, it is assumed that an imaging device can receive signals and emit a volume source detectable by a detector. Under such a circumstance, the aforesaid G can be simplified as a matrix depicting the geometric relationship, where gij stands for the geometric detection effect of the i-th voxel with respect to the j-th detector. For the detectors are disposed at different positions, the received signals would be different in a possibility view. Thus, the possibility information shall be fed back to the reconstruction process so as to amend the difference in spatial distribution.

In the foregoing equation, the computation of a big matrix is time-consuming and thus forms a bottleneck. For example, if the f is a 512×512×512 3D image having n=134217728 image pixels and apply a 3072×3072 detector to perform a 360-degree imaging by a sampling rate of each 1 degree increment., then m=3072×3072×360 and the matrix dimension would be 3397386240×134217728~4.56e+17. Limited by the computation resources of the computer, the question of how to precisely depict the system and how to apply the concept of the sparse matrix to reduce the calculation time of the computer has become a challenge in applications of the iterative reconstruction.

In current art, the ray tracing is usually applied to resolve the aforesaid question. Further, a program optimization application is proposed by Siddon R L (1985). Therefore, various image-processing techniques based on the ray tracing are now developing, such as the technique to simulate the travelling trace of the photon in a defined space, the technique to investigate the crystal penetrability and so on. By having the computed tomography as an example, where the light source and the detector are assumed to be volumeless, and the center of light source and the center of the detector are defined as two fixed points. Through the light-beam connection between these two fixed points to depict the imaging, the possibility is defined to be the length of the light beam that crosses the voxels of the image in the space, and the gij for image reconstruction is defined as the ratio of the length of a light beam passing the voxel to the length of the whole imaging space. It is clear that the effect on the imaging by the volumes of the light source and the detector has been overlooked. Also, in order to obtain higher resolution, when the voxel is smaller than a detector in volume, the effect of the voxel on the imaging might be neglected. To have this problem be resolved, a means of increasing the number of the light beams can be applied; namely, by segmenting the mathematic model of the detector further so as to reduce the effect of the detector's volume upon the calculation. For example, in a document of Huesman R H (2000), each of the two detection units is cut into 3×3 so as to increase the total number of the light beams to 729 times (for the light beams are received by pairs). Though the slope and the ratio of the light beams can be compressed and simplified, yet the improvement therefrom is a trade-off subjected to the $O(n^4)$ algorithm. Therefore, the ray tracing pattern may simplify the model and have advantages in calculation, yet the requirements in more sub-rays for reconstructing and more computation time for increasing the imaging precision would form a barrier to inhibit its practice.

In addition, another resort thereof is to assume the voxel into a sphere. A typical name for such a resort is the spherically symmetric volume elements (blobs). By adopting relevant mathematical equations and applying the distance between a point to the spherical center, the density inside the sphere can be adjusted. This technical resort is usually applied to an imaging process that needs a higher resolution. For example, in an article by Marabini R L (1998), this resort is applied to an electron microscope. Nevertheless, the computation time related to this resort would be huge, and thus the application thereof can be seen in the academic research or in the simulation, but seldom in the industry.

Commercially, a popular method uses the ray tracing technique in cooperating with the interpolation. This improved technique is also called as a ray driven or pixel driven technique. In this resort, a weighting rearrangement has been processed through an interpolating consideration in distances, from which no more data loss in compressing the z-directional information caused by neglecting any voxel in the concerned space would happen. (It is well known that the aforesaid data loss will lead to more bias for imaging under a larger angle.)

To meet the precision requirement in image reconstruction and to avoid cost hike in calculation of time-consuming iterative reconstruction, the analytical methods are usually the inevitable choices in the current marketplace. Hence, the need for developing a new model-based iterative reconstruction algorithm can be foreseen, such as a clustering algorithm for footprints or a parallel accelerating algorithm. Nowadays, some major medical manufacturers also invest money on developing new techniques for the iterative reconstruction method and try to develop a more precise model for researching the iterative reconstruction techniques, so as hopefully to obtain a 3D reconstructed image with a higher resolution but without huge calculations.

SUMMARY OF THE INVENTION

Accordingly, it is the primary object of the present invention to provide a projection method of three-dimensional imaging, by which the calculation time can be substantially reduced.

In the present invention, the projection method of three-dimensional imaging includes the steps of: (a) providing a light source, wherein the light source is to generate a radiation field for being projected onto a detecting module, which includes a plurality of detectors arranged in an array pattern; (b) piling between the light source and the detecting module a plurality of three-dimensional sub-voxels to form a voxel in a form of 3D matrix; (c) defining a sub radiation field between each of the detectors that have detected the radiation field and the light source; (d) basing on each of the three-dimensional sub-voxels in the sub radiation field with respect to each of the detectors to perform a calculation so as to obtain a sub-geometric factor; and, (e) collecting all the sub-geometric factors of the three-dimensional sub-voxels with respect to the individual detectors in the sub radiation field to form a geometric factor matrix. The calculation further includes the steps of: (d1) projecting each of the detectors, the sub radiation field respective to each of the detectors, and the plurality of three-dimensional sub-voxels onto a first detection plane and a second detection plane, respectively, so that each of the detectors, the sub radiation field respective to each of the detectors, and the plurality of three-dimensional sub-voxels form correspondingly a plane detector, a plane radiation field and a plurality of 1D arrays in parallel to further form a two-dimensional plane on the first detection plane and the second detection plane, respectively. Each of the 1D array has a plurality of grids. The first detection plane is expanded by a first axis and a second axis and the second detection plane is expanded by the first axis and a third axis; (d2) rotating the plane detector to the first axis of the first detection plane and the first axis of the second detection plane, respectively, so as to generate a varied coordinate between the plane detector and the plurality of grids; (d3) basing on the varied coordinate to calculate a corresponding geometric ratio value for each of the grids of the plane radiation field with respect to each of the plane detectors which occupies the first detection plane and the second detection plane, respectively; and, (d4) multiplying the two geometric ratio values of each said grid with respect to the first detection plane and the second detection plane so as to obtain the sub-geometric factor of the three-dimensional sub-voxel with respect to each said detector.

In one embodiment of the present invention, the step (d3) further includes the steps of: (d31) locating a plurality of radiation-field intersection points along a calculation pathway for the plane radiation fields with respect to the individual plane detectors on the first detection plane and the second detection plane, respectively, wherein the calculation pathways on the first detection plane and the second detection plane are the second axis of the first detection plane and the third axis of the second detection plane, respectively; (d32) basing on the varied coordinate to locate respectively a plurality of specific intersection points of each individual grid on the calculation pathway with respect to the first detection plane and the second detection plane; and, (d33) performing a calculation for comparing coordinates of a plurality of radiation-field intersection points and coordinates of a plurality of specific intersection points, so as to determine the corresponding geometric ratio value of the individual plane radiation field of each said grid on the calculation pathway with respect to each corresponding plane detector.

In one embodiment of the present invention, after the step (d31) and prior to the step (d32), the projection method of three-dimensional imaging further includes the steps of: (d311) basing on the varied coordinate to calculate proportionally an occupied length of the plane radiation field on the calculation pathway; and (d322) basing on the occupied length of the plane radiation field on the calculation pathway to derive the coordinates of the radiation-field intersection points.

In one embodiment of the present invention, the step (d311) further includes the steps of: (d3111) determining a corresponding first district within the plane radiation field with respect to each of the plane detectors; (d3112) determining a corresponding second district on the calculation pathway within the plane radiation field with respect to each of the plane detectors; and (d3113) basing on the varied coordinate to obtain a ratio of the first district to the second district so as to derive the occupied length of the plane radiation field on the calculation pathway.

In one embodiment of the present invention, prior to performing the step (d33), the projection method of three-dimensional imaging further includes the steps of: (d33a) determining a boundary distance; (d33b) selecting a selected distance on the calculation pathway, wherein the selected distance is larger than or equal to the boundary distance; and, (d33c) within a range of the calculation pathway defined by having the grid as a center and the selected distance as a radius, determining if any specific intersection point is located in the plane radiation field.

In one embodiment of the present invention, the step (d3) further includes a step of multiplying the sub-geometric factor by a weighting factor.

In one embodiment of the present invention, after the step (d4), the projection method of three-dimensional imaging further includes the steps of: (d41) calculating the number of the grids parallel to the first axis on the first detection plane and the second detection plane, respectively; and, (d42) multiplying the sub-geometric factor by a normalized factor, wherein the normalized factor is the ratio of a parameter 1 to the number of the grids.

In one embodiment of the present invention, the light source can further undergo a rotating movement.

In one embodiment of the present invention, the detecting module can be a tomosynthesis, a computed tomography (CT), or the like.

In the present invention, the projection method of three-dimensional imaging is firstly to project a mathematic model originally in the three-dimensional space respectively onto two 2D detection planes, and then to rotate the plane detector to an axis of the corresponding detection plane, such that the related calculation can be simplified and also the calculation time can be reduced.

All these objects are achieved by the projection method of three-dimensional imaging described below.

BRIEF DESCRIPTION OF THE DRAWINGS

The present invention will now be specified with reference to its preferred embodiment illustrated in the drawings, where.

DESCRIPTION OF THE PREFERRED EMBODIMENT

The invention disclosed herein is directed to a projection method of three-dimensional imaging. In the following description, numerous details are set forth in order to provide a thorough understanding of the present invention. It will be appreciated by one skilled in the art that variations of these specific details are possible while still achieving the results of the present invention. In other instance, well-known components are not described in detail in order not to obscure the present invention unnecessarily.

In the present invention, the projection method of three-dimensional imaging is provided to perform image reconstruction for the tomosynthesis, the computed tomography (CT), and the like iterative reconstruction analysis.

Figure 1:
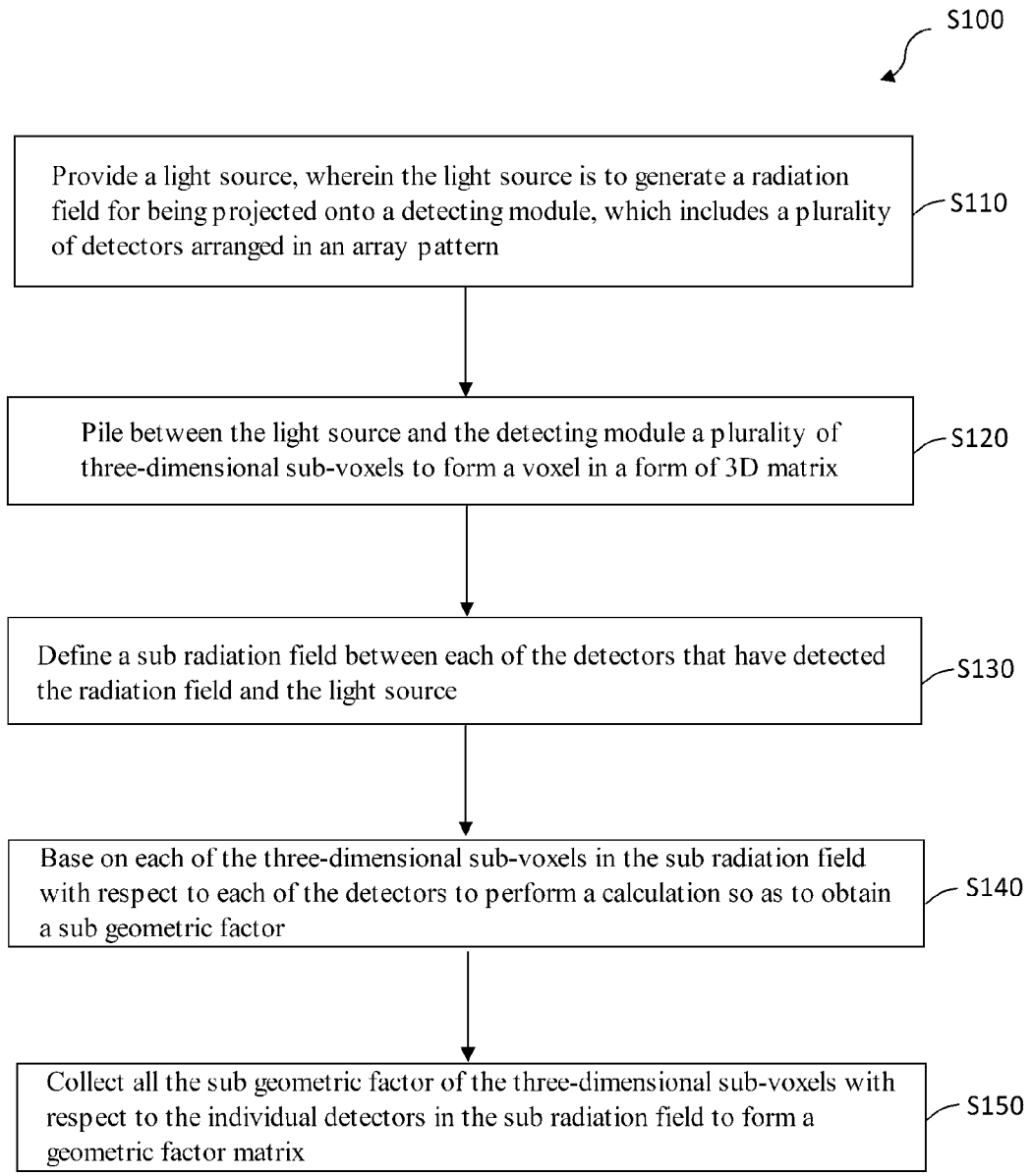
FIG. 1 is a flowchart of the preferred projection method of three-dimensional imaging in accordance with the present invention.
Figure 2:
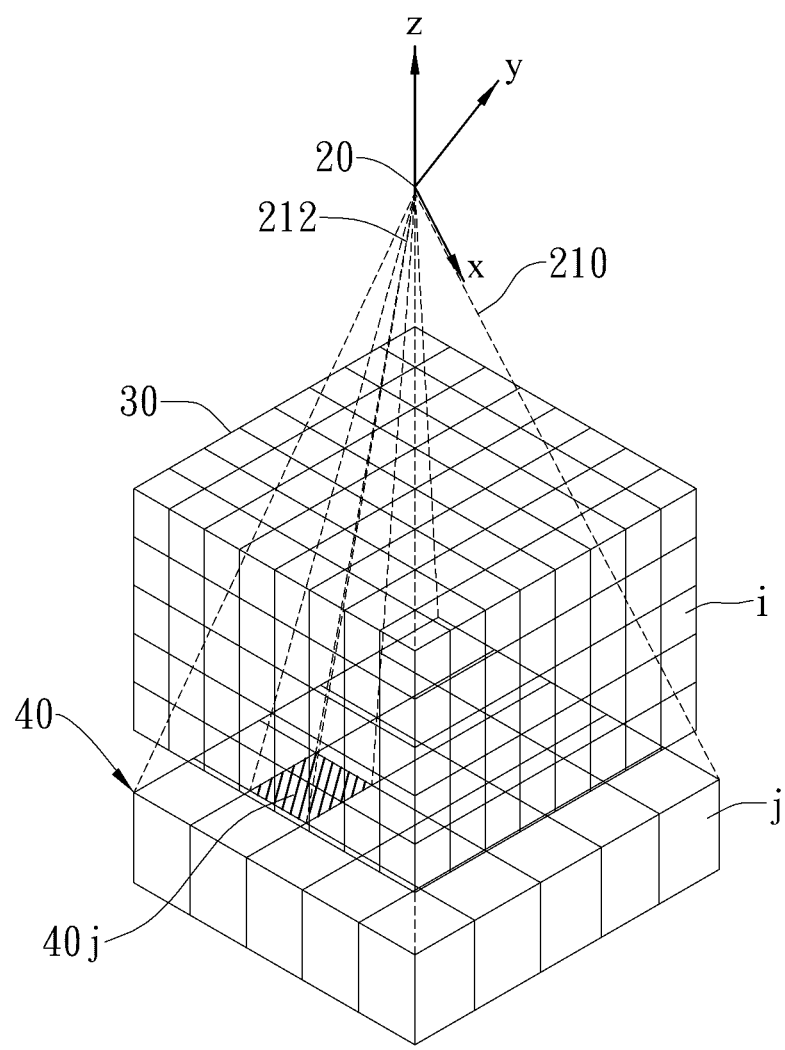
FIG. 2 is a schematic view showing the relationship of a light source and detectors in accordance with the present invention.

Refer now to FIG. 1 and FIG. 2, where FIG. 1 is a flowchart of the preferred projection method of three-dimensional imaging in accordance with the present invention, and FIG. 2 is a schematic view showing the relationship of a light source and detectors in accordance with the present invention. As shown, the projection method of three-dimensional imaging S100 includes the following steps. Firstly, in Step S110, a light source 20 is provided to generate a corresponding radiation field 210 for being projected onto a detecting module 40, where the detecting module 40 includes a plurality of detectors j arranged in an array pattern.

In this embodiment, the light source 20 can be a light source to generate the X rays. The detecting module 40 is to detect the X rays generated by the light source 20. In the present invention, the light source 20 is not limited to the X-ray source, but is defined according to practical application requirements. In addition, in one embodiment of the present invention, the light source 20 can further undergo a rotating movement so as to rotate around the object to be detected and the detecting module 40. However, the present invention shall not be limited the aforesaid embodiment, but shall be relevantly embodied according to practical application requirements. Further, in this embodiment, the detecting module 40. Also, the detecting module of the present invention shall not be limited the aforesaid embodiment, but be relevantly embodied according to practical application requirements.

Then, perform Step S120 to pile between the light source 20 and the detecting module 40 a plurality of three-dimensional sub-voxels i, such that a voxel 30 in a form of 3D matrix can be produced.

Practically, as shown in FIG. 2, this embodiment is to construct a three-dimensional space defined with a first axis Z, a second axis X and a third axis Y between the light source 20 and the plurality of the detectors j arranged in an array pattern. Further, in this three-dimensional space, a plurality of three-dimensional sub-voxels i are piled to form a voxel 30 in a form of a 3D matrix. It shall be noted here that the location to position the light source 20 is not necessarily limited to that shown in FIG. 2. In this embodiment, the light source is particularly to be defined as the origin of the three-dimensional space, i.e. the major reference center point in order to simplify the calculation. Then, in Step S130, define a sub radiation field 212 between the light source and each of the detectors j that have detected the radiation field 210, where the sub radiation field 212 is a portion of the radiation field 210 and is extended between the light source 20 and the corresponding detector j.

Then, Step S140 is to perform a calculation of sub-geometric factor gij based on each of the three-dimensional sub-voxels i in the sub radiation field 212 with respect to each of the detector j.

Figure 3:
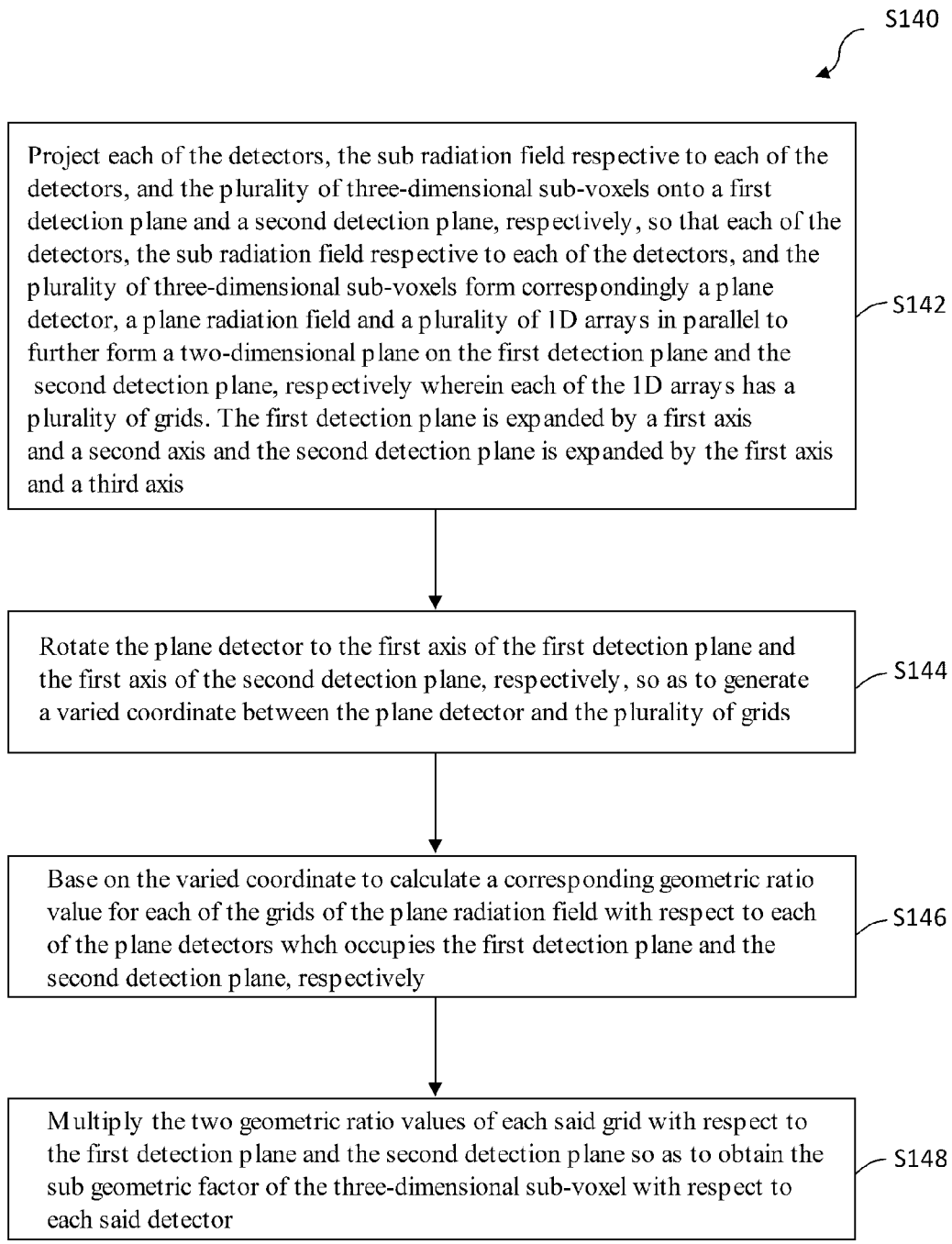
FIG. 3 is a flowchart for calculating the sub-geometric factor of FIG. 1.

FIG. 3 is a flowchart for calculating the sub-geometric factor of FIG. 1. Refer now to FIG. 3 and FIG. 2. The aforesaid calculation in Step S140 includes in details Step S142 to Step S148 of FIG. 3. In Step S142, project the detector j, the sub radiation field 212 respective to the detector j, and the plurality of three-dimensional sub-voxels i onto a first detection plane P1 and a second detection plane P2, respectively, where the first detection plane P1 is a -X-Z plane and the second detection plane P2 is a Y-Z plane. It shall be noted that the aforesaid two axes for each detection planes are selected arbitrarily from the three axes: the first axis Z, the second axis X and the third axis Y. However, in the present invention, such a selection shall not be limited the aforesaid embodiment, but shall be relevantly embodied according to practical application requirements.

Figure 4A:
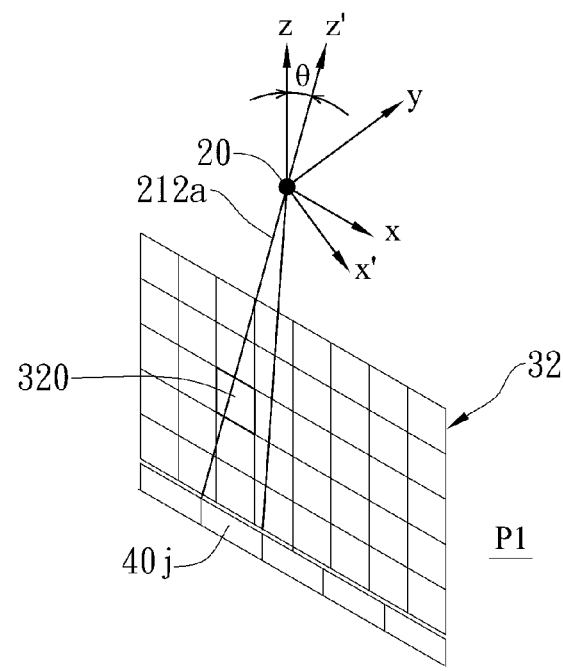
FIG. 4A demonstrates schematically a projection of the sub radiation field and the three-dimensional sub-voxels of FIG. 2 onto a first detection plane in accordance with the present invention.
Figure 4B:
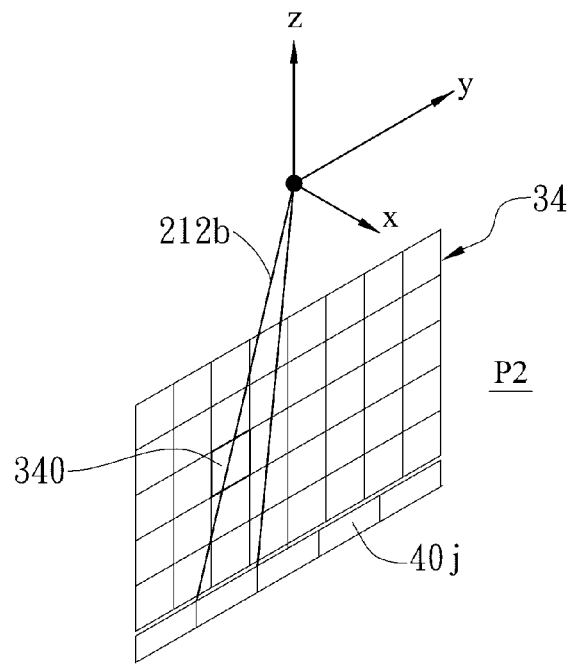
FIG. 4B demonstrates schematically a projection of the sub radiation field and the three-dimensional sub-voxels of FIG. 2 onto a second detection plane in accordance with the present invention.

FIG. 4A demonstrates schematically a projection of the sub radiation field and the three-dimensional sub-voxels of FIG. 2 onto a first detection plane P1 in accordance with the present invention, and FIG. 4B demonstrates schematically a projection of the sub radiation field and the three-dimensional sub-voxels of FIG. 2 onto a second detection plane P2 in accordance with the present invention. Following Step S142, after the projection onto the first detection plane P1 (X-Z plane) shown in FIG. 4A, the detector j, the sub radiation field 212 respective to the detector j, and the plurality of three-dimensional sub-voxels i of FIG. 2 form respectively a plane detector 40j, a plane radiation field 212a and a plurality of 1D arrays 32 in parallel to further form a two-dimensional plane on the first detection plane P1, where each of the 1D arrays 32 has a plurality of grids 320.

Similarly, after the projection onto the second detection plane P2 (Y-Z plane) shown in FIG. 4B, the detector j, the sub radiation field 212 respective to the detector j, and the plurality of three-dimensional sub-voxels i of FIG. 2 form respectively a plane detector 40j, a plane radiation field 212b and a plurality of 1D arrays 34 in parallel to further form a two-dimensional plane on the second detection plane P2, where each of the 1D arrays 34 has a plurality of grids 340.

As described above, in this embodiment, the projection model (i.e. the detector j, the sub radiation field 212 respective to the detector j, and the plurality of three-dimensional sub-voxels i) is projected onto the first detection plane P1 (i.e. the X-Z plane) and the second detection plane P2 (i.e. the Y-Z plane). In particularly, each of the three-dimensional sub-voxels i of FIG. 2 is corresponding to an individual grid 320 on the first detection plane P1 of FIG. 4A, and each of the three-dimensional sub-voxels i of FIG. 2 is corresponding to an individual grid 340 on the second detection plane P2 of FIG. 4B.

Referring back to FIG. 3, in Step S144, each of the plane detectors 40j is rotated to the first axis Z of the first detection plane P1 and the first axis Z of the second detection plane P2. Namely, on the first detection plane P1, each individual plane detector 40j is rotated to the first axis, and, similarly on the second detection plane P2, each individual plane detector 40j is rotated to the first axis Z.

In the aforesaid Steps, the projection method of three-dimensional imaging S100 of the present invention is to project the mathematic model in the three-dimensional space onto the two 2D detection planes, and further to rotate the plane detectors 40j to the corresponding first axis Z so as to simplify the calculations and thus further to reduce the time for the calculations. In other embodiments in accordance with the present invention, a treatment of rotating the plane detector 40j on the first detection plane P1 to the second axis X and the plane detector 40j on the second detection plane P2 to the third axis Y can also be applied to achieve the aforesaid object of simplifying the calculations. Obviously, aforesaid projection and rotation in accordance with the present invention shall not be limited to the aforesaid embodiment, but shall be relevantly embodied according to practical calculation requirements.

In the following description, the explanation of the method of the present invention would be elucidated particularly by having the first detection plane P1 and the corresponding rotation of the plane detector 40j to the first axis Z as the example.

Figure 5:
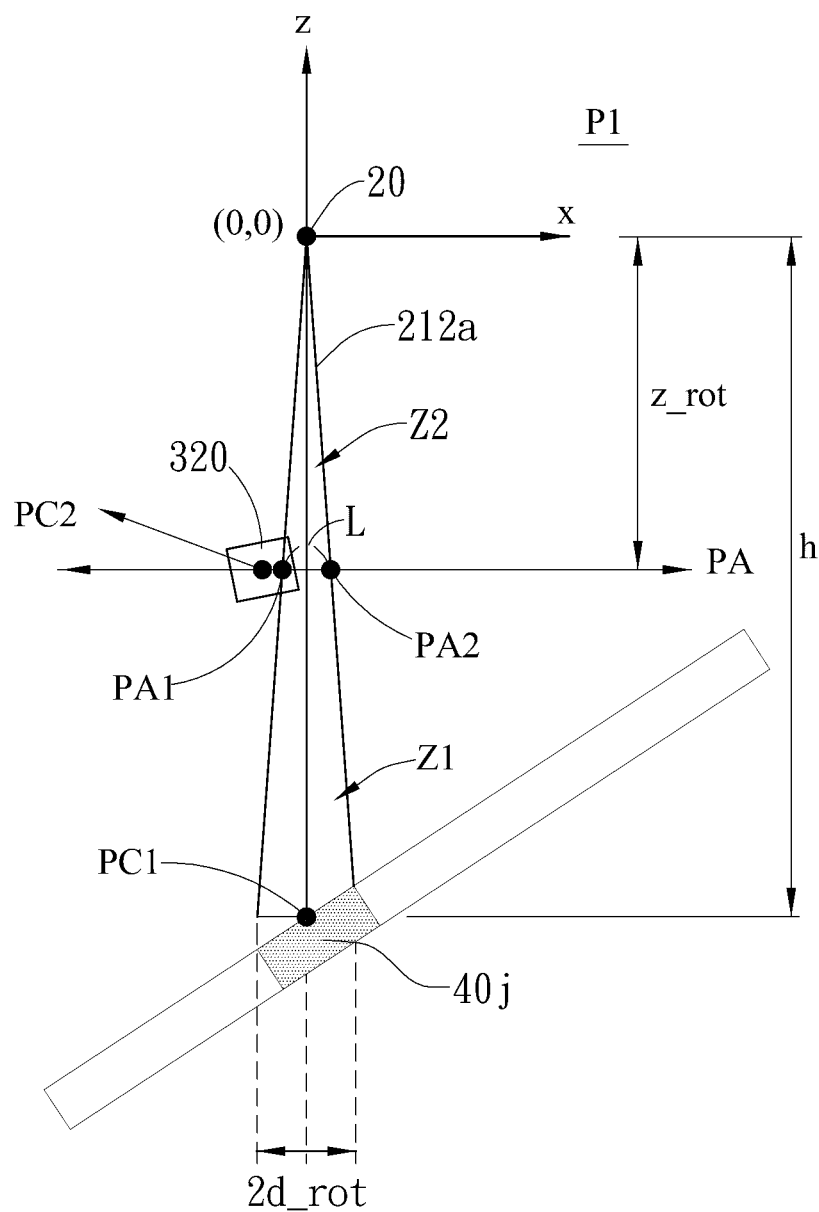
FIG. 5 is a schematic view demonstrating the rotation of the plane detector of FIG. 4A to a first axis.

FIG. 5 is a schematic view demonstrating the rotation of the plane detector of FIG. 4A to the first axis. Refer now to FIG. 4A and FIG. 5. It shall be noted that, in order to explain concisely the present invention, FIG. 5 shows only a typical grid 320 on first detection plane P1 of FIG. 4A, where the light source 20 is defined as the origin (0,0).

In this embodiment, on the first detection plane P1, the plane detector 40j is rotated to the first axis Z so as to have the plane detector 40j and the plurality of grids 320 to generate a corresponding varied coordinate.

For example, as shown in FIG. 4A, a surface center point PC1 of the plane detector 40j has a coordinate (u,w), the surface center point PC2 of the grid 320 has a coordinate (x',z'), and an angle is formed between the Z' axis and the first axis Z.

As shown in FIG. 5, after the plane detector 40j is rotated to the first axis Z, the coordinate (u,w) for the surface center point PC1 of the plane detector 40j would be transformed into a varied coordinate (0,h), and the coordinate (x',z') for the surface center point PC2 of the grid 320 would be transformed into a varied coordinate (x_rot, z_rot), where the variable h is the distance between the light source 20 to the surface center point PC1 of the plane detector 40j.

In details, the aforesaid rotation of the plane detector 40j to the first axis Z is performed by multiplying the corresponding sin or cos of the trigonometric function. Thereby, the coordinate (x',z') for the surface center point PC2 of the grid 320 would be rotated to the varied coordinate (x_rot, z_rot). The related mathematical expressions for the aforesaid transformation are listed as follows.

$$x\_rot = x' \cos\theta - z' \sin\theta \qquad (1)$$

$$z\_rot = x' \sin\theta + z' \cos\theta \qquad (2)$$

Certainly, in the case that the plane detector 40j is rotated to the second axis X or the third axis Y, expressions similar to the mathematical expressions (1) and (2) can be derived according to the trigonometric theorems.

Refer back to FIG. 3 again. In Step S146, base on the varied coordinates individually to calculate the corresponding geometric ratio values for the grids of the respective plane radiation field with respect to the plane detectors that occupy the first detection plane P1 and the second detection plane P2, respectively. In this Step S146, parallel calculations with respect to the first and the second detection planes can be performed. Namely, calculations for the first detection plane P1 and the second detection plane P2 can be processed simultaneously. However, it is also acceptable to process the first detection plane P1 first and then to process the second detection plane P2 later; or, to process the second detection plane P2 first and then to process the first detection plane P1 later. However, the present invention shall not be limited the aforesaid embodiment, but shall be relevantly embodied according to practical application requirements.

Figure 6:
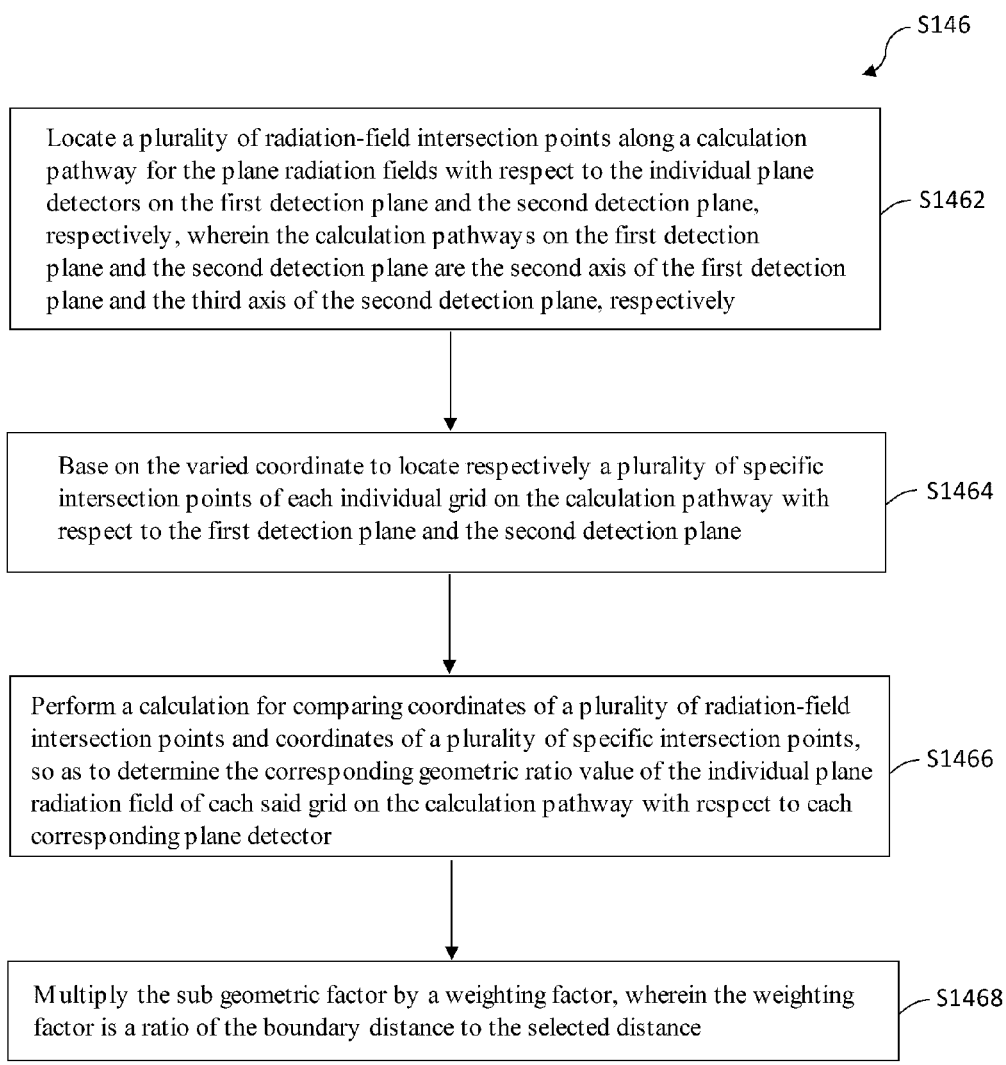
FIG. 6 is a flowchart for calculating the geometric ratio value in accordance with the present invention.

Referring now to FIG. 6, a flowchart for calculating the geometric ratio value in accordance with the present invention is shown. In Step S1462, a plurality of radiation-field intersection points along a calculation pathway for the plane radiation fields with respect to the individual plane detectors are located on the first detection plane and the second detection plane, respectively. In the aforesaid calculations, the calculation pathways on the first detection plane and the second detection plane are the second axis of the first detection plane and the third axis of the second detection plane, respectively.

By having the first detection plane P1 as an example, please refer now back to FIG. 5. Firstly, locate the first radiation-field intersection point PA1 and the second radiation-field intersection point PA2 for the plane radiation fields 212a on a calculation pathway PA with respect to the plane detector 40j on the first detection plane P1, where the calculation pathway PA on the first detection plane P1 is parallel to the second axis X of the first detection plane P1. Equally, in Step S144, the plane detector 40j is rotated to the second axis X, and then the aforesaid calculation pathway on the first detection plane shall now be parallel to the first axis Z of the first detection plane P1.

In other embodiments, if the second detection plane P2 is considered, the plane detector 40j is then rotated to the first axis Z, and now the calculation pathway on the second detection plane P2 would be parallel to the third axis Y of the second detection plane P2. Equally, if the plane detector 40j is rotated to the third axis Y, then the calculation pathway on the second detection plane P2 would be parallel to the first axis Z of the second detection plane P2. However, the present invention shall not be limited the aforesaid embodiment, but be relevantly embodied according to practical application requirements.

Figure 7:
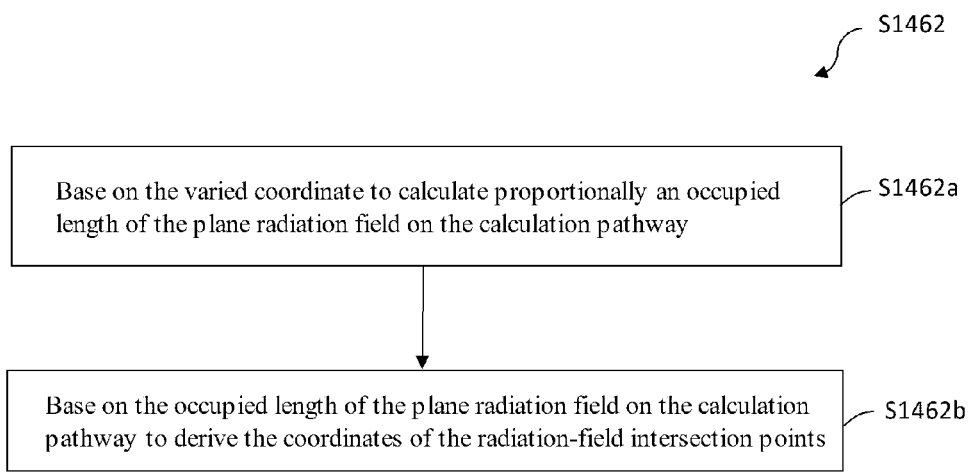
FIG. 7 is a flowchart for calculating the coordinates of the occupied length of the plane radiation field on the calculation pathway and the corresponding radiation-field intersection points in accordance with the present invention.

In addition, after Step S1462 is performed, the projection method of three-dimensional imaging S100 can further include Step S1462a and Step S1462b. FIG. 7 is a flowchart for calculating the occupied length of the plane radiation field on the calculation pathway and the corresponding coordinates of the radiation-field intersection points in accordance with the present invention.

In Step S1462a, base on the varied coordinate to calculate proportionally the occupied length L of the plane radiation field 212a on the calculation pathway PA.

Figure 8:
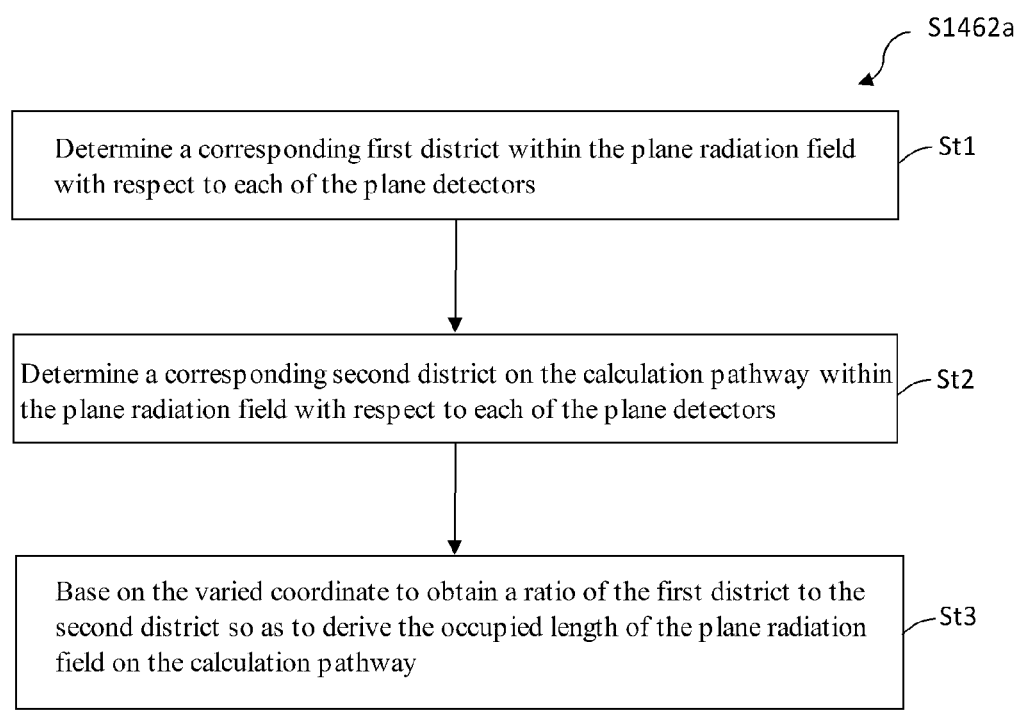
FIG. 8 is a flowchart for calculating proportionally the occupied length of the plane radiation field on the calculation pathway in accordance with the present invention.

Refer now to FIG. 8 and FIG. 5, where FIG. 8 is a flowchart for calculating proportionally the occupied length of the plane radiation field on the calculation pathway.

In Step St1, determine a corresponding first district Z1 within the plane radiation field 212a with respect to each of the plane detectors 40j. Namely, the first district Z1 is the triangle district encircled by the light source 20, the plane radiation field 212a and the plane detector 40j rotated to the first axis Z.

In Step St2, determine a corresponding second district Z2 on the calculation pathway PA within the plane radiation field 212a with respect to each of the plane detectors 40j. Namely, the second district Z2 is the triangle district encircled by the light source 20, the plane radiation field 212a and the calculation pathway PA.

In Step St3, base on the varied coordinate to obtain a ratio of the first district Z1 to the second district Z2 so as to derive the occupied length L of the plane radiation field 212a on the calculation pathway PA.

Referring back to FIG. 5, the varied coordinate of the surface center point PC1 of the plane detector 40j is (0,h), and the varied coordinate of the surface center point PC2 of the grid 320 is (x'_rot, z'_rot). For example, in the case that the detector j has a length 2d, then the length of the plane detector 40j after being rotated to the first axis Z would be 2d_rot. In this calculation, the related modification difference may be expressed by the following mathematical expression.

$$2d\_rot \approx 2d \times \cos\theta \quad (3)$$

In this mathematical expression (3), as the distance goes larger, then the modification difference would become smaller. In practice, the distance between the light source 20 and the detector j is usually comparatively large. Therefore, the aforesaid mathematical expression (3), i.e. the modification difference, would be too small to affect the related calculation.

As described, by comparing the first district Z1 and the second district Z2, the occupied length L of the plane radiation field 212a on the calculation pathway PA can be computed, and the related mathematical equations can be as follows.

$$2d\_rot : L = h : z\_rot \quad (4)$$

$$L = 2d\_rot \times z\_rot / h \quad (5)$$

Referring back to FIG. 7, after the occupied length L of the plane radiation field 212a on the calculation pathway PA is computed in Step S1462a, then, in Step S1462b, base on the occupied length L of the plane radiation field 212a on the calculation pathway PA to derive the coordinates of the radiation-field intersection points.

Referring back to FIG. 5, the radiation-field intersection points are the first radiation-field intersection point PA1 and the second radiation-field intersection point PA2. The occupied length L of the plane radiation field 212a on the calculation pathway PA is the aforesaid distance between the first radiation-field intersection point PA1 and the second radiation-field intersection point PA2. Then, the coordinate for the first radiation-field intersection point PA1 would be (−L/2, z_rot), while the coordinate for the second radiation-field intersection point PA2 would be (L/2, z_rot).

Referring back to FIG. 6, after performing Step S1462 to locate the first radiation-field intersection point PA1 and the second radiation-field intersection point PA2 of the plane radiation field 212a on the calculation pathway PA with respect to the corresponding plane detector 40j, Step S1464 is then performed to base on the varied coordinates to locate respectively a plurality of specific intersection points of each individual grid on the calculation pathway with respect to the first detection plane and the second detection plane.

Figure 9:
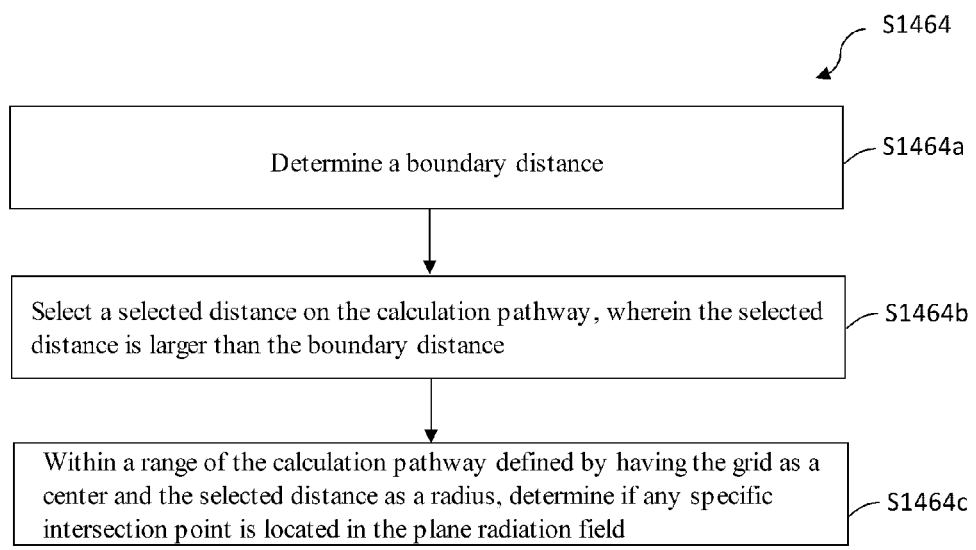
FIG. 9 is a flowchart for locating the specific intersection points on the calculation pathway with respect to the grid on the first detection plane according to the varied coordinate in accordance with the present invention.
Figure 10:
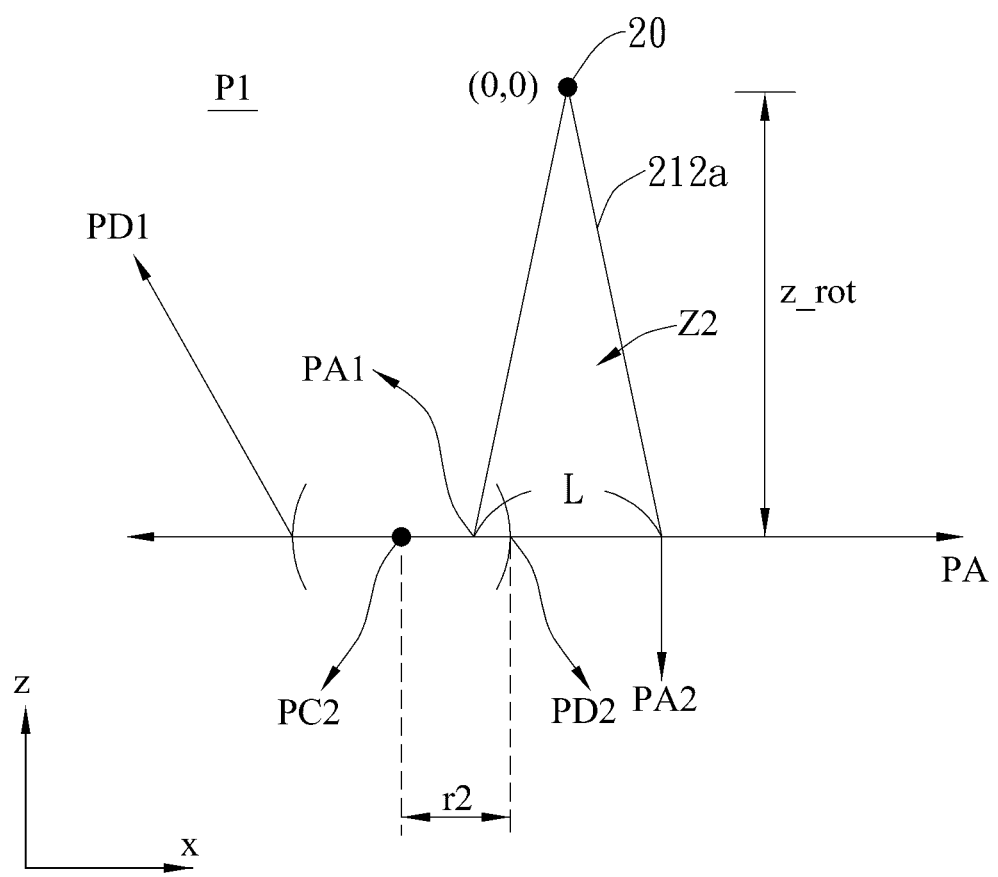
FIG. 10 is a schematic view showing the calculation of lengths for the intersecting segments on the calculation pathway of FIG. 5.

By having the first detection plane P1 as an example, refer now to FIG. 9 and FIG. 10, where FIG. 9 is a flowchart for locating the specific intersection points on the calculation pathway with respect to the grid on the first detection plane according to the varied coordinate in accordance with the present invention, and FIG. 10 is a schematic view showing the calculation for locating the intersecting segments on the calculation pathway of FIG. 5. It shall be noted that FIG. 10 only shows the light source 20, a portion of the plane radiation field 212a and the calculation pathway PA; i.e. the second district Z2.

In Step S1464a, a boundary distance r1 is determined. Then, in Step S1464b, a distance is selected on the calculation pathway PA, and the selected distance is larger than the boundary distance. Then, in Step S1464c, within the range of the calculation pathway defined by having the grid as a center and the selected distance as the radius, determine if any specific intersection point is located in the plane radiation field. As shown in FIG. 10, on the calculation pathway PA, the aforesaid range is defined by having the surface center point PC2 of the grid 320 as the center and the selected distance r2 as the radius, and thus the first specific intersection point PD1 and the second specific intersection point PD2 can be located. Further, from FIG. 10, the varied coordinate of the surface center point PC2 of the grid 320 is (x_rot, z_rot), while the varied coordinate of the first intersection point PD1 is (x_rot−r2, z_rot) and that of the second specific intersection point PD2 is (x_rot+r2, z_rot).

It shall be mentioned is that, in this embodiment, the surface center point of the grid in the voxel is specified for a typical example. However, in other embodiments, a boundary point of the grid in the voxel can also be a reference point. Anyhow, the present invention shall not be limited the aforesaid embodiment, but be relevantly embodied according to practical calculation requirements.

From Step S1464c and FIG. 10, the second specific intersection point PD2 is located inside the range of the plane radiation field 212a. Then, in FIG. 6, Step S1466 is executed to perform a calculation for comparing coordinates of a plurality of radiation-field intersection points and those of a plurality of specific intersection points, so as to determine the corresponding geometric ratio value of the individual plane radiation field of each grid on the calculation pathway with respect to each corresponding plane detector.

Referring to FIG. 10, on the first detection plane PA, the coordinate of the first specific intersection point PD1 is (x_rot−r2, z_rot), that of the second specific intersection point PD2 is (x_rot+r2, z_rot), that of the first radiation-field intersection point PA1 is (−L/2, z_rot), and that of the second radiation-field intersection point PA2 is (L/2, z_rot), where the L is the occupied length of the plane radiation field 212a on the calculation pathway PA. Thus, for the aforesaid specific intersection point and the radiation-field intersection point are both located on the calculation pathway PA, it is enough for the related calculation to simply include the coordinate on the second axis X. The related mathematical equation is listed as follows.

$$g_{xz} = \max(\min(L/2, x\_rot+r2) - \max(-L/2, x\_rot-r2), 0)/L \quad (6)$$

In the aforesaid mathematical equation (6), compare the coordinate of the first radiation-field intersection point PA1 with that of the first specific intersection point PD1 so as to determine the maximum coordinate of the two coordinates, compare the coordinate of the second radiation-field intersection point PA2 with that of the second specific intersection point PD2 so as to determine the minimum coordinate of these two coordinates, then subtract the minimum coordinate from the maximum coordinate and ensure a positive number is obtained, and finally the geometric ratio value gxz of the individual plane radiation field 212a of each grid 320 on the calculation pathway PA of the first detection plane P1 with respect to each corresponding plane detector 40j can be obtained by dividing the aforesaid positive number by the occupied length L of the plane radiation field 212a on the calculation pathway PA.

The similar calculations and processes can be applied to obtain the geometric ratio value gyz with respect to the second detection plane P2.

Referring back to FIG. 3, in performing Step S148, multiply the two geometric ratio values of the grid with respect to the first detection plane P1 and the second detection plane P2 so as to obtain the sub-geometric factor gij of the three-dimensional sub-voxel with respect to each individual detector.

Referring now to FIG. 6, after the aforesaid sub-geometric factor gij is obtained, perform Step S1468 to multiply the sub-geometric factor gij by a weighting factor W, where the calculation of the weighting factor W is explained as follows.

Figure 11A:
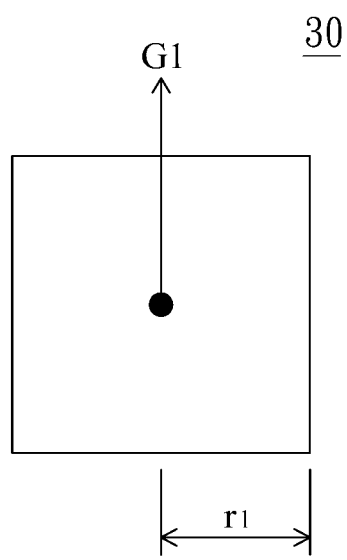
FIG. 11A is a schematic view of a typical sub-voxel in accordance with the present invention.
Figure 11B:
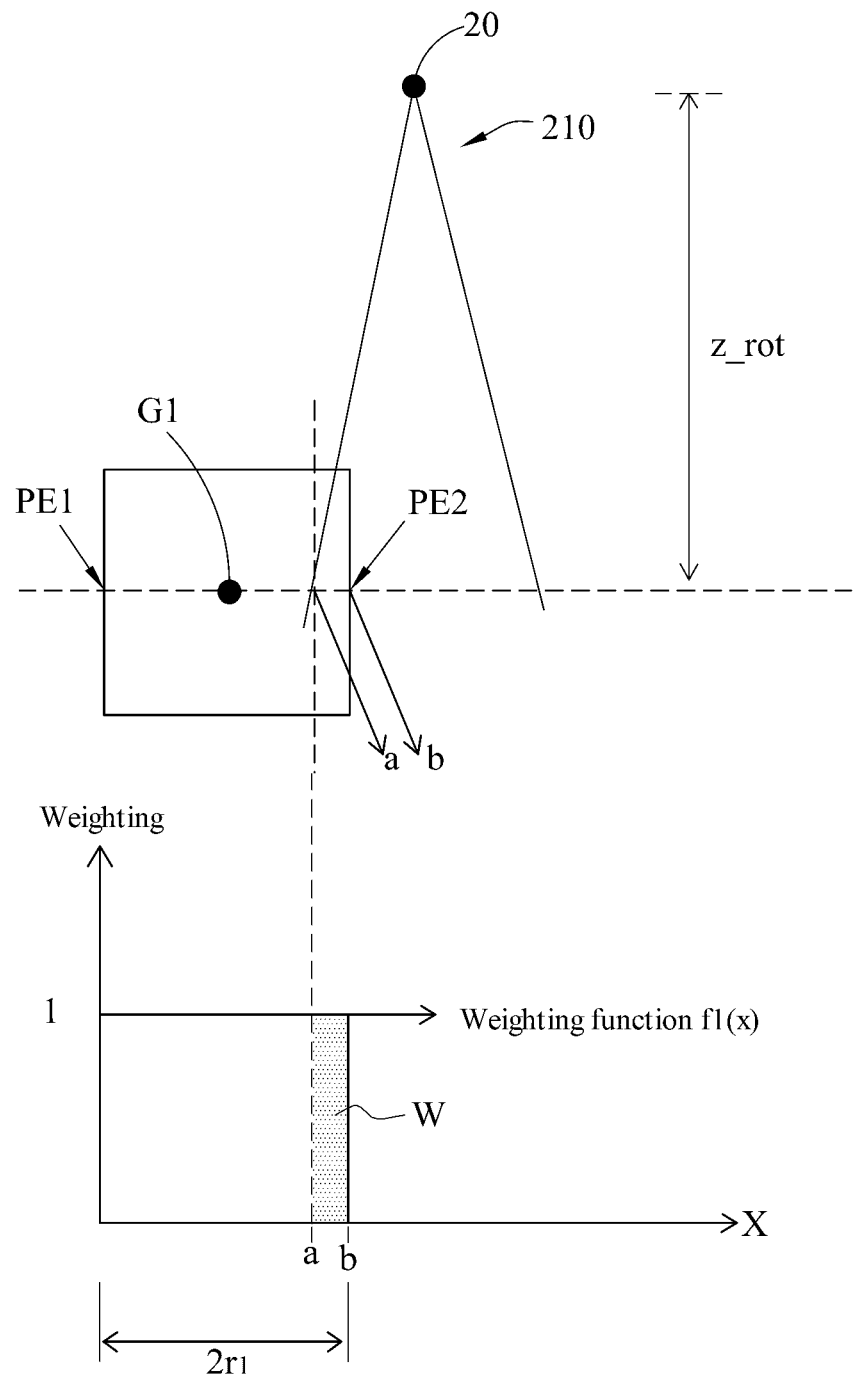
FIG. 11B shows schematically the intersection of the sub-voxel of FIG. 11A and the radiation field.

FIG. 11A is a schematic view of a typical sub-voxel in accordance with the present invention, and FIG. 11B shows schematically the intersection of the sub-voxel of FIG. 11A and the radiation field.

As shown in FIG. 11A, in the aforesaid Step S1464a, the boundary distance r1 is defined. In this embodiment, the vertical distance between the surface center point G1 of the voxel 30 and the boundary of the voxel 30 is defined as the boundary distance r1. As shown in FIG. 11B, the intersection of the un-rotated voxel (or a sub-voxel) of FIG. 11A and the radiation field 210 is schematically shown. If the coordinate of the first crossing point PE1 is (x_rot−r1, z_rot), then the coordinate of the second crossing point PE2 would be (x_rot+r1, z_rot). If the coordinate of the first radiation-field intersection point PA1 is (−L/2, z_rot), then the coordinate of the second radiation-field intersection point PA2 would be (L/2, z_rot). Accordingly, the intersection points of sub-voxel in the radiation field 210 at the second axis X are the first intersection point a and the second intersection point b, where the coordinate of the first intersection point a is (−L/2, z_rot), and the coordinate of the second intersection point b is (x_rot−r1, z_rot). In calculations, a weighting function f1(x) given by the user is adopted. In FIG. 11B, the weighting for the weighting function f1(x) is a constant 1. In the lower portion of FIG. 11B, the area W stands for the possibility of the voxel 30. The calculation of W is listed as follows.

$$(b-a) \times f1(x) = (b-a) \times 1 = b-a = W \quad (7)$$

Obviously, the calculation of the W is equivalent to an integration from the first intersection point a to the second intersection point b, and the total integration value is 2×r1 in this embodiment.

Figure 11C:
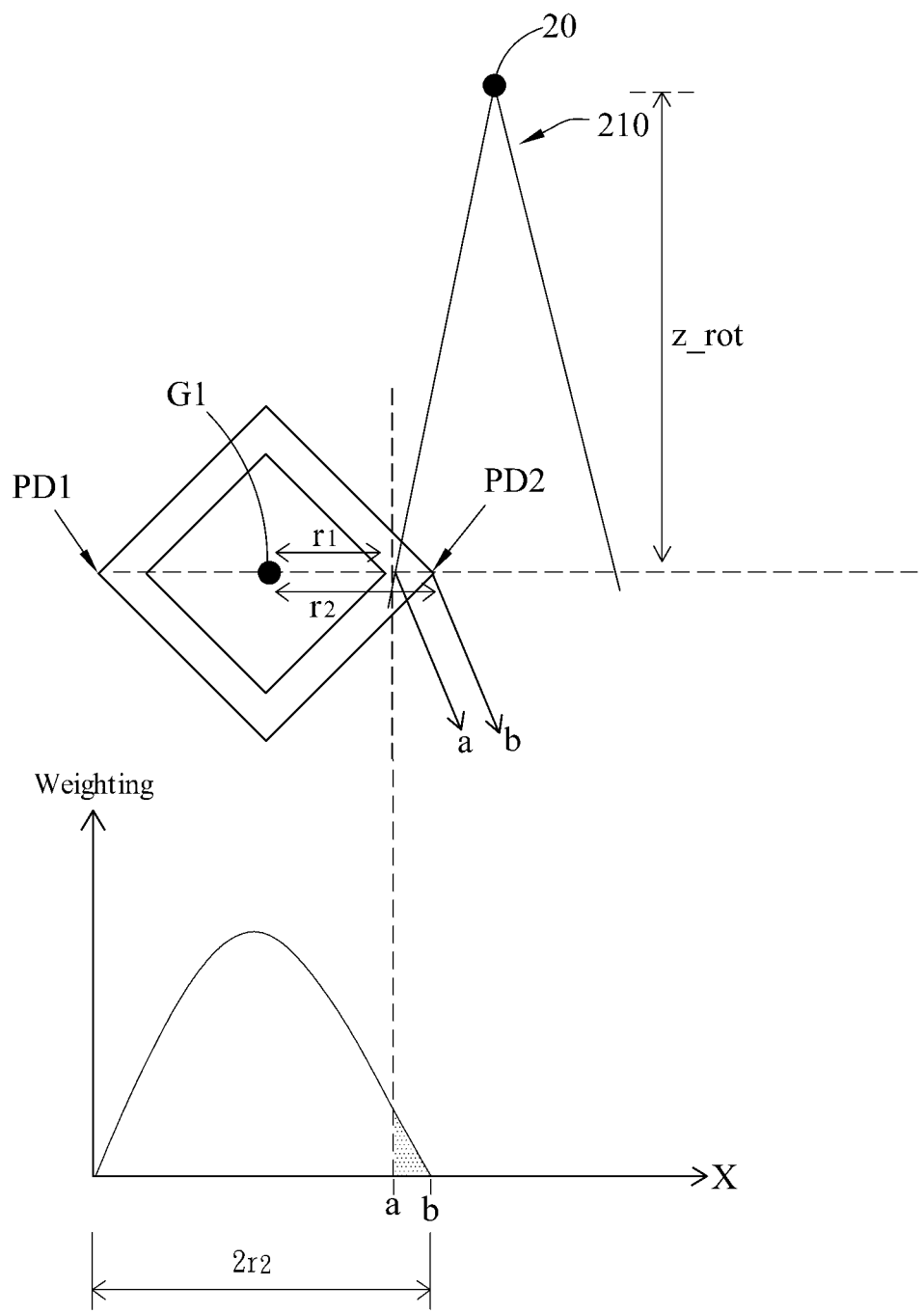
FIG. 11C shows schematically the intersection of a rotated sub-voxel of FIG. 11A and the radiation field.

In practice, the voxel 30 is to be rotated. FIG. 11C shows schematically the intersection of a rotated voxel (sub-voxel) of FIG. 11A and the radiation field. At this time, if the aforesaid boundary distance r1 is adopted for calculations, it is quite possible that no intersection in between with the radiation field 210 can be found, and results in computational errors.

Hence, in this embodiment, a selected distance r2 is defined to be larger than the boundary distance r1. If the coordinate of the first specific intersection point PD1 is (x_rot−r2, z_rot), then the coordinate of the second specific intersection point PD2 would be (x_rot+r2, z_rot). In calculations, a weighting function f2(x) given by the user is adopted. In FIG. 11C, the weighting function f2(x) is related to the rotational angle. In the lower portion of FIG. 11C, the integral area is computed from the first intersection point a to the second intersection point b.

It shall be noted that, no matter what the weighting function is, the total integration by adopting any kind of the weighting functions shall be identical. For example, the total integration is 2×r1 in both FIG. 11B and FIG. 11C.

In practice, a table for various pairs of the first intersection point a and the second intersection point b can be established in advance. Then, the computation for obtaining the weighting factor W can simply be a step of looking up table.

Upon such an arrangement, if the voxel 30 is not rotated, the boundary distance can be r1 and the weighting function f1(x) can be the constant 1. Then, the weighting factor W according to the mathematical equation (7) is simply the (b−a) value. Further, if the aforesaid selected distance r2 is larger than the boundary distance r1, the weighting factor W can be obtained by directly looking up the table, such that the calculation loading related to the selected distance r2 can be substantially reduced.

Figure 12:
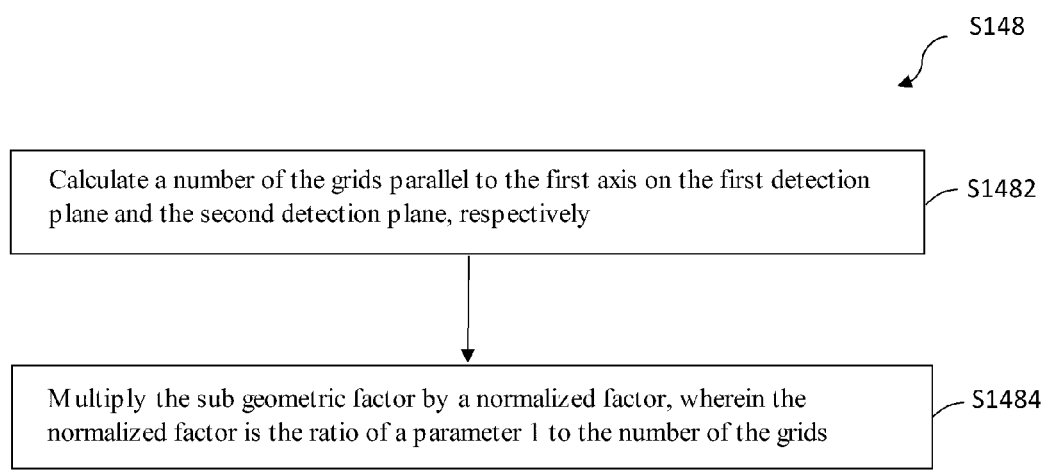
FIG. 12 is a flowchart for calculating the normalized factor for the projection method of three-dimensional imaging in accordance with the present invention.

In addition, after Step S148 is performed, the embodiment of the projection method of three-dimensional imaging can further include the following steps of:

Referring now to FIG. 12, a flowchart for calculating the normalized factor for the projection method of three-dimensional imaging in accordance with the present invention is shown. In Step S1482, perform calculations of the number of the grids parallel to the first axis on the first detection plane and the second detection plane, respectively. In this embodiment, as shown in FIG. 2, the number of the grids on the first axis Z is 5.

Then, in Step S1484, the sub-geometric factor is further multiplied by a normalized factor, where the normalized factor is the ratio of the parameter 1 to the number of the grids. In this embodiment, the normalized factor N is 1/5.

Referring back to FIG. 1, after performing Step S140 and the following Steps, the sub-geometric factor gij can be obtained. Finally, Step S150 is performed to collect all the sub-geometric factors gij of the corresponding three-dimensional sub-voxels i with respect to the individual detectors j in the sub radiation field 212, which form the geometric factor matrix G.

In summary, the projection method of three-dimensional imaging provided by the present invention is to derive the geometric factors required for reconstructing medical image in the field of the radiological medicine. In the present invention, a mathematic model originally in the three-dimensional space is projected respectively onto two 2D detection planes, and then the plane detector is rotated to an axis of the corresponding detection plane, such that the related calculation can be simplified and also the calculation time can be reduced.

While the present invention has been particularly shown and described with reference to a preferred embodiment, it will be understood by those skilled in the art that various changes in form and detail may be without departing from the spirit and scope of the present invention.

What is claimed is:

1. A projection method of three-dimensional imaging, comprising the steps of:
   (a) providing a light source, wherein the light source is to generate a radiation field for being projected onto a detecting module, which includes a plurality of detectors arranged in an array pattern;
   (b) piling between the light source and the detecting module a plurality of three-dimensional sub-voxels to form a voxel in a form of 3D matrix;
   (c) defining a sub radiation field between each of the detectors that have detected the radiation field and the light source;
   (d) basing on each of the three-dimensional sub-voxels in the sub radiation field with respect to each of the detectors to perform a calculation so as to obtain a sub-geometric factor, the calculation further comprising the steps of:
   (d1) projecting each of the detectors, the sub radiation field respective to each of the detectors, and the plurality of three-dimensional sub-voxels onto a first detection plane and a second detection plane, respectively, so that each of the detectors, the sub radiation field respective to each of the detectors, and the plurality of three-dimensional sub-voxels form correspondingly a plane detector, a plane radiation field and a plurality of 1D arrays in parallel to further form a two-dimensional plane on the first detection plane and the second detection plane, respectively; wherein each of the 1D arrays has a plurality of grids, and wherein the first detection plane is expanded by a first axis and a second axis and the second detection plane is expanded by the first axis and a third axis;
   (d2) rotating the plane detector to the first axis of the first detection plane and the first axis of the second detection plane, respectively, so as to generate a varied coordinate between the plane detector and the plurality of grids;
   (d3) basing on the varied coordinate to calculate a corresponding geometric ratio value for each of the grids of the plane radiation field with respect to each of the plane detectors to occupy the first detection plane and the second detection plane, respectively; and
   (d4) multiplying the two geometric ratio values of each said grid with respect to the first detection plane and the second detection plane so as to obtain the sub-geometric factor of the three-dimensional sub-voxel with respect to each said detector; and
   (e) collecting all the sub-geometric factors of the three-dimensional sub-voxels with respect to the individual detectors in the sub radiation field to form a geometric factor matrix.

2. The projection method of three-dimensional imaging of claim 1, wherein the step (d3) further includes the steps of:
   (d31) locating a plurality of radiation-field intersection points along a calculation pathway for the plane radiation fields with respect to the individual plane detectors on the first detection plane and the second detection plane, respectively, wherein the calculation pathways on the first detection plane and the second detection plane are the second axis of the first detection plane and the third axis of the second detection plane, respectively;
   (d32) basing on the varied coordinate to locate respectively a plurality of specific intersection points of each individual grid on the calculation pathway with respect to the first detection plane and the second detection plane; and
   (d33) performing a calculation for comparing coordinates of a plurality of radiation-field intersection points and coordinates of a plurality of specific intersection points, so as to determine the corresponding geometric ratio value of the individual plane radiation field of each said grid on the calculation pathway with respect to each corresponding plane detector.

3. The projection method of three-dimensional imaging of claim 2, after the step (d31) and prior to the step (d32), further including the steps of:
   (d311) basing on the varied coordinate to calculate proportionally an occupied length of the plane radiation field on the calculation pathway; and
   (d322) basing on the occupied length of the plane radiation field on the calculation pathway to derive the coordinates of the radiation-field intersection points.

4. The projection method of three-dimensional imaging of claim 3, wherein the step (d311) further includes the steps of:
   (d3111) determining a corresponding first district within the plane radiation field with respect to each of the plane detectors;
   (d3112) determining a corresponding second district on the calculation pathway within the plane radiation field with respect to each of the plane detectors; and
   (d3113) basing on the varied coordinate to obtain a ratio of the first district to the second district so as to derive the occupied length of the plane radiation field on the calculation pathway.

5. The projection method of three-dimensional imaging of claim 2, prior to performing the step (d33), further including the steps of:

(d33a) determining a boundary distance;
(d33b) selecting a selected distance on the calculation pathway, wherein the selected distance is larger than the boundary distance; and
(d33c) within a range of the calculation pathway defined by having the grid as a center and the selected distance as a radius, determining if any specific intersection point is located in the plane radiation field.

6. The projection method of three-dimensional imaging of claim 2, further including a step of:
multiplying the sub-geometric factor by a weighting factor.

7. The projection method of three-dimensional imaging of claim 1, after the step (d4), further including the steps of:
(d41) calculating a number of the grids parallel to the first axis on the first detection plane and the second detection plane, respectively; and
(d42) multiplying the sub-geometric factor by a normalized factor, wherein the normalized factor is the ratio of a parameter 1 to the number of the grids.

8. The projection method of three-dimensional imaging of claim 1, wherein the light source further undergoes a rotating movement.

9. The projection method of three-dimensional imaging of claim 1, wherein the detecting module is one of a tomosynthesis and a computed tomography.

* * * * *